| United States Patent [19] | [11] Patent Number: 5,037,918 |
|---|---|
| Babb | [45] Date of Patent: Aug. 6, 1991 |

[54] PERFLUOROCYCLOBUTANE RING-CONTAINING POLYMERS WITH CROSSLINKING

[75] Inventor: David A. Babb, Lake Jackson, Tex.

[73] Assignee: The Dow Chemical Company, Midland, Mich.

[21] Appl. No.: 451,404

[22] Filed: Dec. 15, 1989

[51] Int. Cl.$^5$ ............................................. C06F 14/18
[52] U.S. Cl. ..................... 526/242; 526/243; 526/245; 526/248; 526/250; 526/251; 526/252; 526/253; 526/255; 526/247; 528/86; 568/669
[58] Field of Search .............. 526/252, 242, 243, 245, 526/247, 248, 250, 251, 253, 255; 528/86; 568/669

[56] References Cited

U.S. PATENT DOCUMENTS

| | | |
|---|---|---|
| 2,404,374 | 7/1946 | Harmon . |
| 2,671,799 | 3/1954 | Miller . |
| 2,848,504 | 8/1958 | Dixon . |
| 2,922,823 | 1/1960 | Tarrant . |
| 2,958,685 | 11/1960 | Sousa . |
| 2,982,786 | 5/1961 | McCane . |
| 3,022,356 | 2/1962 | Nooy . |
| 3,111,509 | 11/1963 | Folt . |
| 3,114,778 | 12/1963 | Fritz et al. . |
| 3,277,068 | 10/1966 | Wall et al. . |
| 3,303,145 | 2/1967 | Carlson . |
| 3,310,606 | 3/1967 | Fritz . |
| 3,316,312 | 4/1967 | McCane et al. . |
| 3,505,411 | 4/1970 | Rice . |
| 3,549,606 | 12/1970 | Gash . |
| 3,682,876 | 8/1972 | Anderson et al. . |
| 3,696,154 | 10/1972 | Anderson . |
| 3,840,603 | 10/1974 | Anderson et al. . |
| 3,900,380 | 8/1975 | Anderson et al. . |
| 3,926,989 | 12/1975 | Rebsdat et al. . |
| 4,154,753 | 5/1979 | Fielding . |
| 4,377,711 | 3/1983 | Rico et al. . |
| 4,423,249 | 12/1983 | Carl et al. . |

FOREIGN PATENT DOCUMENTS

| | | |
|---|---|---|
| 303292 | 2/1989 | European Pat. Off. . |
| 1126554 | 5/1968 | United Kingdom . |
| 1185564 | 3/1970 | United Kingdom . |
| 8602072 | 4/1986 | World Int. Prop. O. . |

OTHER PUBLICATIONS

Paleta et al., "Haloacrylic Acids VI. Ethylene Glycol Bis(Trifluoroacrylate)" Sb. Vsy. Sk. Chem. Technol. 1976, C23, 5-11 (1976).
A. A. Glazkov et al. Bulletin of the Academy of Sciences of the USSR vol. 37, No. 10 Part 2.
P. Tarrant et al., J. Org. Chem. vol. 31, No. 4, 1966, pp. 1143-6.
Chemical Abstract 105:171569h.
Chemical Abstract 59:8879c.
Chemical Abstract 77:34091k.
Chemical Abstracts 110:181626.
Henne and Ruh in *J. Amer. Chem. Soc.*, 69, 279-281 (1947).
Maurice Prober in *J. Amer. Chem. Soc.*, 75, 968-973 (1953).
Hauptschein et al. in *J. Amer. Chem. Soc.*, 79 2549-2553 (1957).
Miller et al. in *J. Amer. Chem. Soc.*, 83, 1767-1768 (1961).
Brown et al. in *J. Poly. Sci. Part A-1*, vol. 3, (1965) pp. 1641-1660.
Brown et al. in *J. Poly. Sci. Part A-1*, vol. 4 (1966) pp. 131-1140.
Banks, et al. in *J. Chem. Soc (C)*, 22 (1966) pp. 2051-2052.
Sharkey in *Fluorine Chem. Rev.* 2, 1-53 (1968).
Crawford in *J. Chem. Soc. (C)*, 1967 pp. 2395-2396.
Hodgdon and Macdonald in *J. Poly. Sci. Part A-1*, vol. 6, (1968) pp. 711-717.
Chambers in *Fluorine in Organic Chemistry*, John Wiley, New York, (1973) pp. 173-191 and 199-208.
Rico and Waselman in *J. Fluorine Chemistry*, 20 (1982) pp. 759-764.
Heinze and Burton in *J. Org. Chem.* 1988, 53, pp. 2714-2720.
Drysdale, Gilbert, Sinclair and Sharkey *J. Amer. Chem. Soc.* vol. 80(1958) pp. 3672-3675.
Coffman, Barrick, Cramer and Raasch in *J. Amer. Chem. Soc.* vol. 71 (1949) 490-496.
McBee, Hsu, Pierce and Roberts in "Diels-Alder Reactions with Fluorine-Containing Olefins" in *J. Amer. Chem. Soc.*, vol. 77 (1955) pp. 915-917.
Chambon and Winter in *J. of Rheology* 31 (1987) pp. 683-697.
Perry in *Fluorine Chemistry Reviews* 1 (2) (1967) pp. 253-313.
Nijenhuis and Winter in *Macromolecules* 22 (1989) pp. 411-414.
Winter and Chambon in *J. of Rheology*, 30(2) (1986) pp. 367-382.

*Primary Examiner*—Paul R. Michl
*Assistant Examiner*—Thomas McDonald

[57] ABSTRACT

A crosslinked polymer having perfluorocyclobutane rings is prepared in a process comprising the steps of: (a) contacting monomers having two dimerizable perfluorovinyl groups; (b) exposing the monomers to sufficient heat and for a sufficient time that a (linear) polymer containing perfluorocyclobutane rings is formed; and (c) exposing the polymer to sufficient crosslinking initiating means and for a sufficient time such that crosslinking occurs. Crosslinked polymers, so prepared are novel and have tensile strength and other physical properties enhanced over the properties of the corresponding linear polymer.

32 Claims, No Drawings

PERFLUOROCYCLOBUTANE RING-CONTAINING POLYMERS WITH CROSSLINKING

This invention relates to crosslinked polymers having perfluorocyclobutane rings, and to thermal processes to prepare such polymers.

Dimerization of certain perfluorovinyl compounds has been reported and is discussed, for instance, in Chambers, *Fluorine in Organic Chemistry,* John Wiley, New York, 1973, pp. 173-191; S. Patai, *The Chemistry of Alkenes,* Wiley Interscience Publishers, 1964, p. 779; M. Hudlicky, *Chemistry of Organic Fluorine Compounds,* 2nd ed., Halsted Press (John Wiley and Sons), 1972, p. 450; and Tarrant ed., *Fluorine Chemistry Reviews,* Vol. 2, Marcel Dekker, 1968 pp. 1-52. In general, the dimerizations are easily sterically hindered and have not been used to prepare long chain molecules. A report of dimerization linking two molecules of such compounds as perfluoropropylene and perfluoropentene-1, included speculation that the reaction could be used for perfluoroalkyl perfluorovinyl compounds wherein the alkyl radical has 1 to 20, "or even a higher number" of carbon atoms. See, McCone et al., U.S. Pat. No. 3,316,312.

Certain polymers having perfluorocyclobutane groups in their backbone and monomers suitable for preparing such polymers are disclosed in copending U.S. Application Ser. Nos. 364,667 filed June 9, 1989; U.S. Application Ser. No. 364,666 filed June 9, 1989: U.S. Application Ser. No. 364,686 filed June 9, 1989: U.S. Application Ser. No. 364,665 filed June 9, 1989. Polymers are prepared from monomers containing more than one perfluorovinyl group. Such polymers are generally linear and thermoplastic except when the polymers are prepared from monomers having more than two perfluorovinyl groups per molecule. In most instances, use of even small amounts of monomers containing more than two of the perfluorovinyl groups results in polymers having crosslinked or branched molecular structures. These crosslinked or branched polymers generally have enhanced mechanical properties as compared to their thermoplastic counterparts, such as tensile strength and modulus and flexural strength and modulus. Such crosslinked or branched polymers are not, however, generally thermally processable, such as by injection molding or extruding, as are the thermoplastics.

It would be desirable to produce a polymer containing perfluorocyclobutane rings which polymer could be thermally processed as a thermoplastic then cured into a crosslinked polymer.

SUMMARY OF THE INVENTION

In one aspect, the invention is a process for preparing a crosslinked polymer having perfluorocyclobutane rings comprising the steps of:
(a) contacting monomers having two dimerizable perfluorovinyl groups:
(b) exposing the monomers to sufficient heat and for a sufficient time that a polymer containing perfluorooyclobutane rings is formed: and
(c) exposing the polymer to sufficient crosslinking initiating means and for a sufficient time such that crosslinking occurs.

In another aspect, the invention is a crosslinked polymer produced by that process.

The crosslinked polymers are advantageously elastomeric in the range from their glass transition temperatures to the temperatures at which degradation is observed, which is generally on the order of 400–450° C. Compared to their thermoplastic counterparts, the crosslinked polymers exhibit enhanced solvent resistance and increased mechanical strength, without loss of advantageous electrical properties, such as low dielectric constant and dissipation factor.

DETAILED DESCRIPTION OF THE INVENTION

Polymers are formed by thermal reaction of monomers having two dimerizable perfluorovinyl groups such that perfluorocyclobutane groups are formed. A dimerizable perfluorovinyl group is a perfluorovinyl group which reacts with another such group to form a perfluorocyclobutane ring. Thus, resulting polymers have at least two perfluorocyclobutane groups. The term polymer is used herein to refer to any compound having at least two perfluorocyclobutane groups formed from perfluorovinyl groups, and includes oligomers which have from about 2 to about 100 repeating units and preferably have a molecular weight of from about 300 to about 30,000. Depending on the molecular structure connecting the perfluorocyclobutyl groups, the number of perfluorocyclobutane groups can vary from as few as two up to thousands.

Any monomer having two dimerizable perfluorovinyl groups and which monomer is thermally polymerizable into crosslinkable polymers is suitably used in the practice of the invention. Whereas polyaddition of perfluorovinyl groups to form perfluoroaliphatic polymers (like polytetrafluoroethylene), not generally having perfluorocyclobutane groups, takes place in the presence of free radicals or free radical generating catalysts, dimerization to form perfluorocyclobutane groups takes place thermally. In the thermal polymerization of diperfluorovinyl compounds, substantially linear polymers having little branching are believed to be formed. In the practice of this invention, certain of these substantially linear polymers are crosslinked. Crosslinking involves chemical reactions that interconnect polymer molecules. As these reactions proceed, a polymer network is formed. Early in a crosslinking process, there are molecules having a wide variety of molecular weights: molecular weight increases with increasing extent of crosslinking. At a point in the progress of crosslinking, the gel point is reached. This point is defined as the point when there is sufficient crosslinking that the polymer is no longer soluble in a solvent for the corresponding uncrosslinked linear polymer. Rather, the polymer swells in the solvent. Theoretically, either the weight average molecular weight diverges to infinity in an infinite sample, or a first macromolecular cluster grows to be on the order of the sample size when the sample is finite. At the gel point, the polymer system loses its solubility and a steady-shear viscosity approaches infinity. A decrease in percent elongation as measured by the procedure of ASTM D882-83 is also observed. Preferably, the decrease in percent elongation is at least about 10 percent, more preferably at least about 20 percent of the percent elongation. At the gel point, there are still unattached polymer molecules within a polymer network system. As these molecules are crosslinked into the network, stiffness increases and the mechanical strength of the polymer (e.g. as measured by the procedures of ASTM D882-83 and ASTM D790-81) is enhanced. The viscosity also continues to increase. The gel point at a temperature can be determined rheologically by the process of H. H. Winter et al. in *J. Rheology*, 30(2), 367-382 (1986) and 31(8), 683-697, (1987); and *Macromolecules*, 22, 411-414, (1989). As measured by the procedure taught by Winters, crosslinked polymers of this invention preferably have gel points within about two hours at about 360° C., more preferably in less than about two hours at 320° C., most preferably in less than about two hours at 280° C. Measurements at temperatures below about 320° C. are more indicative of a preferred crosslinking because crosslinking at such temperatures is accompanied by thermal decomposition.

Before crosslinking, solid polymers of the invention are generally thermoplastic. Viscosity of either a melt or solution of the polymer increases as crosslinking occurs until the gel point and resulting unsolubility is reached. The crosslinked polymers are preferably elastomeric, that is, the polymer can generally regain its shape after deformation. That deformation is indicated by elongation measurements greater than about 100% at temperatures above the glass transition temperature (Tg) of the polymer. The crosslinked polymers preferably retain their elastomeric properties at temperatures of from their glass transition temperatures to the temperatures at which they are observed to degrade, preferably about 400° C. The glass transition temperature varies with the composition of the polymer.

Crosslinking also increases a polymer's tensile strength as measured by the procedures of ASTM D882-83. The increase is preferably up to about 1000%, more preferably from about 10% to about 500%, most preferably of from about 10% to about 100% increase. Also the polymer's tensile and flexural modulus as measured by the procedures of ASTM D882-83 and ASTM D790-81, respectively, also increases, preferably up to about 1,000%, more preferably of from about 10% to about 500%, most preferably of from about 10% to about 100%. Additionally, the fluorine-containing structures of such crosslinked polymers preferably retain relatively low dielectric constants.

Although any monomer having two dimerizable perfluorovinyl groups and which is crosslinkable is suitably used, crosslinked polymers of the invention are preferably prepared from monomers having two perfluorovinyl groups separated by at least one hydrocarbyl group having at least one carbon atom between the perfluorovinyl groups.

Furthermore, when the perfluorovinyl groups are attached to aliphatic carbons or separated from aliphatic carbons by single atoms such as oxygen, the perfluorovinyl groups are preferably primary or secondary because tertiary perfluorovinyl groups are generally sterically hindered with respect to formation of perfluorocyclobutane rings, more preferably the perfluorovinyl groups are primary because secondary perfluorovinyl groups tend to rearrange. Preferably, to avoid rearrangement and facilitate polymer formation and crosslinking the monomers have structures such that resulting polymers have hydrocarbyl groups (preferably aromatic rings), perfluorocyclobutane rings and at least one non-carbon atom such as oxygen, silicon, boron, phosphorus, nitrogen, selenium, tellurium and/or sulfur atom (each optionally substituted) in the backbones.

The monomers preferably have a structure represented by Formula I:

$$CF_2=CF-X-R-X-CF=CF_2$$

wherein R represents an, optionally inertly substituted group; and each X is independently a bond or any group which links R and a perfluorovinyl group (hereinafter linking structures), said structures being inert. By "inert" it is meant that the structures or substituents do not react undesirably with perfluorovinyl groups or interfere undesirably with polymerization (perfluorocyclobutane formation) of the monomers.

Linking structures X are each independently a linking structure such as a bond, an oxygen atom, carboxylic and thiocarboxylic ester groups, other sulfur containing structures, perfluoroalkylene, perfluoroalkylene ether, alkylene, acetylene, phosphorus containing groups such as phosphines, carbonyl and thio carbonyl groups: seleno: telluro: nitrido: silicon-containing groups such as silanediyl, trisilanediyl tetrasilanetetrayl, siloxanediyl, disiloxanediyl, trisiloxyl, trisilazanyl, or silylthio groups; boron-containing groups such as boranediyl or methylboranediyl groups; a combination thereof, or any other group which is inert, which molecularly links R to a perfluorovinyl group, and which provides a molecular structure in which the perfluorovinyl group is sufficiently reactive to form a perfluorocyclobutane ring. For instance, X is preferably other than a perfluoroalkylene group because perfluorovinyl groups attached to perfluoroalkylene groups generally require temperatures greater than about 300° C. to dimerize and are subject to isomerization.

It is preferred that at least one of X is not a bond. More preferably, X is independently selected from the group consisting of groups having at least one non-carbon atom between the perfluorovinyl groups and R, such as groups containing oxygen, sulfur, selenium atoms, tellurium atoms, silicon, boron, phosphorus or nitrogen between R and the perfluorovinyl group, e.g. oxygen atoms, sulfur atoms, (thio) carboxylic ester groups, phosphines, (thio) carbonyl groups, seleno, telluro, silanediyl, trisilanediyl, trisilazanyl or silylthio, boranediyl groups. Preferred groups have S, O, Si, N or P, more preferably S, 0, or Si between R and the perfluorovinyl group, such as carbonyl, thiocarbonyl, sulfone, sulfoxy, silanediyl, amines (optionally inertly substituted), oxygen or sulfur atoms. Most preferably there is a single atom other than carbon: even more preferably it is oxygen or sulfur, among those groups preferably an ether or sulfide linkage, because monomers having such linking structures advantageously form perfluorocyclobutane groups at lower temperatures than are needed with such groups as perfluoroalkyl groups and are more stable than monomers where the perfluorovinyl group is attached directly to R, particularly when R is aromatic. Monomers having such linking structures are also relatively easily prepared.

R is suitably any inert molecular structure, preferably a molecular structure which facilitates formation of perfluorocyclobutane rings or crosslinking and/or imparts desirable physical properties to polymers or oligomers prepared from the monomers. For the purpose of imparting desirable physical properties to polymers, R preferably contains at least one carbon atom in the molecular chain between X's because monomers having at least one carbon atom between X's when X is other than a bond, tend to have desirable stability and to produce polymers having desirable physical properties. Alternatively, the carbon atom is in a side chain: for instance, —R— can be —N(CH₃)—, —N(CH₂CH₃)—P(CH₃)—, —P(CH₂CH₃)— and the like. Carbon atoms(s) in R are suitably in aliphatic, cycloaliphatic, aromatic, heterocyclic groups and the like and combinations thereof. Additionally, R optionally contains groups or has substituents which are inert, that is which do not undesirably interfere with the formation of crosslinks or perfluorocyclobutane rings from perfluorovinyl groups. Inert substituents include ether, carbonyl, ester, tertiary amide, carbonate, sulfide, sulfoxide, sulfone, nitrile, alkyl phosphonate, tertiary amine, alkyl phosphate, alkyl silyl, chlorine, bromine, fluorine, alkyl, arylalkyl, alkylaryl, cycloalkyl, aromatic, heterocyclic, alkoxyl, aryloxy groups and the like, which inert substituents are suitably in any position, for instance, in a polymer backbone between X's and/or appended to such a backbone. Carbon-containing inert substituents on R preferably contain from about 1 to about 50, more preferably from about 1 to about 12 carbon atoms because of the stability and ease of working with monomers of lower molecular weight. R, including inert substituents preferably has a molecular weight (MW) of from about 14 to about 20,000, more preferably from about 75 to about 15,000 and most preferably from about 75 to about 5,000. These ranges include monomeric and oligomeric R groups. In the case of monomers which are other than oligomeric, R preferably has from about 1 to about 50, more preferably from about 6 to about 25, carbon atoms because molecular weights above this reduce the contribution to properties made by the fluorine-containing substituents when R is alkyl or aromatic hydrocarbon. As previously discussed, the nature of R as well as the perfluorocyclobutane content of the polymers can vary broadly according to the type of products desired.

Preferably, for polymers having good plastic properties such as tensile strength and flexibility, at least one carbon atom of R is in the molecular chain between X's and is part of an aromatic nucleus. Aromatic groups are desirable because of improved physical properties of the polymers and ease of manufacture of the monomers. For both ease of manufacture of the monomer and monomer stability, when R is aromatic, each X is preferably independently sulfur or oxygen. The aromatic group can be any molecular structure having aromatic character, advantageously having at least one six membered aromatic ring, suitably having any number of such six-membered rings fused together or connected by bonds or linking structures. R preferably has from about 1 to about 50 such rings, more preferably from about 1 to about 10 rings, more preferably containing from about 6 to about 25 carbon atoms, most preferably R has at least 2 to about 4 aromatic rings to impart properties such as hardness and/or stiffness to a polymer. The aromatic fragment is suitably unsubstituted or inertly substituted. Inert substituents on an aromatic R include, for instance, the inert substituents listed for R generally. Exemplary aromatic molecular fragments include, for instance, perchlorophenylene, phenylene, biphenylene, naphthylene, dichlorophenylene, nitrophenylene, p,p'(2,2-diphenylene propane) [—C₆H₄—C(CH₃)₂—C₆H₄]; p,p'-(2,2-diphenylene -1,1,1,3,3,3 hexafluoropropane) [—C₆H₄—C(CF₃)₂—C₆H₄—], preferably biphenylene: phenylene; 9,9'-diphenylfluorene, oxydiphenylene: thiodiphenylene; 2,2-diphenylene propane: 2,2'-diphenylene, 1,1,1,3,3,3-hexafluoropropane; 1,1-diphenylene-1-phenylethane; naphthalene; and anthracene.

For the purpose of facilitating crosslinking, more preferably, R is a group which reacts with perfluorovinyl groups residual in a substantially linear polymer to form a crosslinked or branched molecular structure. The reaction of R with the perfluorovinyl groups is suitably initiated by heat, free radicals, wave energy, or any other crosslinking initiating means, but preferably by heat. Most preferably R includes a structure having two double, triple or aromatic bonds (hereafter multiple bonds) separated by a single bond. Such structures are recognized in the art as latent dienes. Preferably the latent dienes are suitable for reactions of the Diels-Alder type, more preferably suitable for such reactions with perfluorovinyl groups in the monomers, most preferably suitable for such reactions with perfluorovinyl ether groups under conditions used for crosslinking. The single bond is preferably a carbon to carbon single bond. Each of the multiple bonds is independently suitably a multiple bond between any two atoms, preferably between a carbon atom and any other atom (e.g. —C═O, —C═C—, —C≡N) more preferably a carbon to carbon bond. Exemplary of preferred R groups include, for instance, biphenylene, 9.9'-diphenylfluorene, flourene, cyclopentadienylene, furan and anthracene.

Even though Diels-Alder reactions of perfluorovinyl groups are rare (See D. D. Coffman, et al., *J. Am. Chem. Soc.*. 71, 490–496 (1949); E. T. McBee, et al., *J. Am. Chem. Soc.*, 77, 915–917 (1955); J. J. Drysdale, et al., *J. Am. Chem. Soc.*, 80, 3672–3675 (1958)), monomers capable of such reactions are observed to give crosslinked polymers having gel points at temperatures generally lower than similar polymers formed from monomers wherein double bonds are separated by more than one single bond.

Most preferably, R has aromatic carbon atoms at least one of which is bonded directly to X, most preferably aromatic carbon atoms of R are bonded directly to each X because perfluorovinyl groups bonded to X, said X being bonded to aromatic groups are generally more reactive in forming perfluorocyclobutane rings.

Some specific combinations of X and R are especially preferred: when R is aromatic, at least one X is preferably other than a bond, more preferably neither X is a bond, because attachment of perfluorovinyl groups directly to aromatic R renders the perfluorovinyl groups more thermally and oxidatively unstable than when said groups are attached, for instance to oxygen or sulfur. When R is a perfluoroalkyl group or a perfluoroalkylether group, at least one X is preferably other than a bond, most preferably no X is a bond or a perfluoroalkyl group, because perfluorovinyl groups linked directly to perfluoroalkyl groups require temperature in excess of about 300° C. to dimerize and are subject to isomerization.

Monomers useful in the practice of the invention are suitably prepared by any method which links molecular structures having perfluorovinyl groups to other molecular structures or which forms perfluorovinyl groups.

Monomers are preferably prepared by the process taught in copending application U.S. Application Ser. No. 364,665 filed June 9, 1989 and incorporated herein in its entirety.

Before crosslinking, substantially linear polymers or oligomers thermally produced from the preferred monomers preferably have a repeating unit formula represented by Formula II wherein R and X are

—[X—R—X—Q]ₙ— defined above; Q is a perfluorocyclobutane group and n is an integer representing the number of repeating units, which is preferably from about 2 to about 100,000, more preferably from about 2 to about 10,000, most preferably from about 3 to about 5,000. Polymer chains of these lengths are terminated by residual perfluorovinyl groups unless the vinyl groups have reacted with other materials.

To form such polymers, the monomers are heated to a temperature and for a time sufficient to form perfluorocyclobutane rings. Temperatures suitable for forming perfluorocyclobutane rings differ with the structure of the monomer. In general, temperatures above about 40° C. are suitable for formation of perfluorocyclobutane rings, preferably the temperature is above about 50° C., more preferably above about 100° C., because these temperatures result in formation of the rings at successively faster rates. Temperatures above about 450° C. are preferably avoided because perfluorocyclobutane groups are generally thermally unstable above such temperatures. More preferably a temperature of from about 105° C. to about 350° C., most preferably from about 105° C. to about 250° C., is used to produce the perfluorocyclobutane rings at a convenient rate. Within that range, a temperature of from about 100° to about 230° is generally most preferred for cyclization of perfluorovinyl aromatic or aliphatic ethers or sulfides, while a temperature of from about 50° C. to 80° C. is needed to form perfluorocyclobutane groups when the perfluorovinyl group is attached directly to an aromatic ring. In the case of perfluoroalkylperfluorovinyl groups, however, temperature of at least about 300° C., preferably at least about 350° C., is generally required. Details of the polymerization process are given in U.S. Application Ser. No. 364,667 filed June 9, 1989 (Attorney Docket No. C-37,374), which is incorporated herein in its entirety.

Polymers prepared by such a process are suitably solids, fluids or gels, preferably solids or fluids, most preferably solids. The solids preferably maintain plastic characteristics such as tensile strength well above ambient temperatures (e.g. above about 25° C.) and have glass transition temperatures from well below ambient to well above ambient temperatures. A particularly preferred group of such polymers have glass transition temperatures (Tg) above ambient (25° C.), preferably above 60° C. and most preferably above 100° C. In general, the polymers having Tg above ambient result from monomers of Formula I wherein R is aromatic, and the polymers having Tg above 60° C. when R contains more than one aromatic ring. A particular desirable property of polymers where R is aromatic and not substituted with polar substituents (e.g. nitro, sulfonate, carboxy) is the combination of good physical properties and good electrical properties. Dielectric constants and static dissipation factors (as measured according to the procedures of ASTM D150-87) preferably range from about 2.2 to about 3.0 and from about 0.0002 to about 0.005 respectively. Glass transition temperatures increase from about ambient when R is phenyl to about 170° C. when R is biphenyl to 230° C. when R is 9,9-diphenylfluorene.

Such polymers can be crosslinked by any crosslinking initiating means such as by heat, by free radicals, or by wave energy. This crosslinking preferably occurs substantially without crosslinking agents such as monomers having three or more functional groups reactive to form the polymers (trifluorovinyl groups). By substantially without, it is meant that while materials which act as crosslinking agents or catalysts for crosslinking may incidentally be present in very small quantities, preferably less than about 0.01 weight percent of the polymer, more preferably less than about 0.01 weight percent crosslinking agent and less than about 0.001 weight percent catalyst for crosslinking, such materials are not deliberately added. Free radicals are suitably provided by use of any means of supplying free radicals such as by use of compounds known in the art for producing free radicals, e.g. organic azo compounds. Wave energy is suitably supplied by means such as ultraviolet light, radiant heat (e.g. infrared light), microwaves, X-rays, or particle beam radiation. Such means are within the skill in the art. Neither thermal crosslinking nor crosslinking using wave energy require addition of a catalyst such as a free radical initiator and such methods are, therefore, preferred. Thermal crosslinking is, however, more preferred.

Thermally crosslinked polymers are prepared from such thermally formed polymers containing perfluorocyclobutane rings by heating the polymers to a temperature sufficient to result in crosslinking, that is for chemical bonds to form between at least some of the polymer molecules. The temperature for such crosslinking is higher than that required for thermal (linear) polymerization, preferably it is at least about 50° C. degrees higher than the temperature required for thermal (linear) polymerization, more preferably from about 250° C. to about 400° C., most preferably from about 280° C. to about 380° C., even more preferably from about 280° C. to about 340° C. These temperatures are suitably maintained for a time sufficient to achieve a preselected degree of crosslinking. Such times are preferably from about 1 minute to about 10 days, more preferably from about 15 minutes to about 1 day (24 hours), most preferably from about 15 minutes to about 8 hours.

A particularly useful aspect of the present invention includes preparing the substantially linear polymers according to processes previously taught and exposing the linear polymer to conditions suitable for crosslinking in a shaping apparatus, e.g. an extruder, a mold, or other apparatus suitable for heating or other crosslinking initiation, e.g. for a time and at a temperature sufficient for crosslinking. This allows handling of a polymer which melts at a relatively lower temperature and producing an elastomer or thermosetting polymer having stability at temperatures sufficient to melt the substantially linear polymer. Crosslinking advantageously occurs without the need for a solvent or a high pressure apparatus, and proceeds without the evolution of volatile compounds or by-products.

Crosslinked polymers formed by the process of the invention differ from crosslinked polymers prepared from monomer mixtures containing monomers having more than two perfluorovinyl groups in that they are prepared directly from bifunctional monomers or thermoplastic polymers thereof without addition of a catalyst or a multifunctional crosslinking agent. Also, polymers prepared from a single monomer having more than one crosslinking agent in general have a very high crosslink density and are more rigid and inflexible solids than polymers crosslinked by the process of the invention.

The following examples are offered to illustrate but not to limit the invention. In each case, percentages are weight percent unless otherwise indicated. Examples (Ex.) of the invention are indicated numerically, while comparative samples (C.S.) are not examples of the invention and are indicated with letters.

All gas chromatography/mass spectrometry (GC/MS) analyses of monomers and intermediates are performed on a Finnigan 1020 GC/MS using a 30 meter RSL-150 fused silica capillary column. All gas chromatography/mass spectrometry (GC/MS) analyses of fluid polymer samples are performed on a Finnigan 4500 GC/MS using a 60 meter DB-1 fused silica capillary column, with the GC program run at 290° C. isothermal. Liquid chromatography/mass spectrometry (LC/MS) is performed on a Finnigan 4500 mass spectrometer using acetonitrile - water eluent and a moving belt LC/MS interface.

Dynamic Mechanical Spectroscopy (DMS) measurements are performed on a Rheometrics RDS-7700 rheometer in parallel plate mode using 25 mm plates at 10% strain and a series of frequencies. Differential scanning calorimetry (DSC), thermomechanical analysis (TMA) and thermogravimetric analysis (TGA) is performed on a Perkin Elmer 7000 thermal analysis system.

Dielectric constant and dissipation factor measurements are conducted according to the procedures of ASTM D150-87. Tensile strength and modulus and percent elongation were measured on an Instron model 1125 according to the procedures of ASTM D-882-83.

Gel Permeation Chromatography (GPC) is performed on a Waters 720 GPC instrument using a methylene chloride eluent and a series of Micro-styragel ® columns of 10,000, 1,000, 500 and 100 angstrom pore sizes. Reported values are standardized against polystyrene.

Granular zinc is activated by washing in 0.1 N hydrochloric acid (HCl) followed by drying in a vacuum oven at 0.5 torr and 140° C. for 10 hours.

Infrared (IR) spectra are measured on a Beckmann Microlab 600 model spectrophotometer. Nuclear Magnetic Resonance (NMR) spectra are measured on a Varian EM360 spectrometer using 19F (fluorine 19) or 1H (hydrogen) mode.

The gel point determination involves a dynamic mechanical spectroscopy technique performed at 10% strain in a parallel plate mode using a 1 mm gap. Storage and loss moduli are measured at frequencies from 0.1 to 100 radians per second, measuring 10 different frequencies per decade of frequency, every 15 minutes. Measurements are carried out isothermally. The ratio of the loss modulus (G'') to the storage modulus (G'), known as the loss tangent, or tan delta (G''/G'), is plotted against time for a number of frequencies. The point at which the value of tan delta becomes independent of frequency (as is indicated by a convergence of plots of the log tan delta vs. time at various frequencies to a point) is known as the gel point, and represents the time at which the size of the polymer chains in the sample increase to a size which is on the order of the size of the sample. At this point the sample is considered crosslinked on a macromolecular scale, and exhibits properties such as enhanced mechanical strength and insolubility in solvents for the thermoplastic precursor.

EXAMPLE 1

PREPARATION, POLYMERIZATION AND CROSSLINKING OF 4,4'-BIS(TRIFLUOROVINYLOXY)BIPHENYL

Dimethyl sulfoxide (DMSO) (1800 ml) is placed in a 5-liter 5-necked flask fitted with a mechanical stirrer, a Dean-Stark phase separating trap topped with a nitrogen padded reflux condenser, and a thermocouple attached to a temperature controller. The solvent is stirred and purged of oxygen by blowing in nitrogen through a dip-tube placed below the surface of the liquid while 4,4'-dihydroxybiphenyl (454g, 2.44 mole) is added to the flask.

The system is stirred and purged for 20 minutes, then potassium hydroxide (85% pellets) (322g, 4.88 mole) is added slowly. The stirred mixture is then heated to 120° C. The temperature is held at 120° C. for 1.5 hours, then the heat is turned off and the mixture is allowed to cool to room temperature. Toluene (600 ml) which has been thoroughly purged with nitrogen is added to the solution and the resulting mixture is heated to reflux (135° C.). Water is azeotropically removed from the reactor through the Dean-Stark trap for a total of 4 days, cooling the reactor once after 24 hours to allow for salt formation to be broken up by opening the flask under a nitrogen sweep and scraping the sides with a spatula. After 4 days the Dean-Stark trap is removed and replaced with a Soxhlet extractor containing anhydrous sodium sulfate. The toluene is then refluxed through the Soxhlet extractor for 7 hours to dry the toluene. After 7 hours, the Soxhlet is replaced with a Dean-Stark trap, and toluene (300 ml) is removed from the reactor by simple distillation. The reaction mixture is then cooled to 30° C. in an ice water bath and 1,2-dibromotetrafluoroethane (1300g, 5.00 mole) is added slowly dropwise over three hours at a rate that maintains a reactor temperature of 35°±2° C. When the addition is complete the reaction temperature is allowed to stabilize (not increasing in temperature when the ice bath is removed) and then a heating mantle is applied to the flask. The reactor is heated to 50° C. for 8 hours, then allowed to cool to room temperature with constant stirring. The crude reaction mixture is filtered to remove the potassium bromide salts, and the precipitate is washed with acetone. The filtrates are combined and thoroughly evaporated to remove acetone, DMSO and residual toluene. The solid residue is subjected to a 2 liter Kugelrohr bulb-to-bulb distillation to provide the crude product. This material is dissolved in 750 ml of methylene chloride and is washed first with mild aqueous potassium bicarbonate (500 ml, approximately. 0.2 M), then with mild aqueous hydrochloric acid (HCl) (500 ml, approximately 0.05 M), then twice with distilled water (500 ml each). After complete phase separation the product layer is removed and evaporated, and the residue is fractionally distilled (138°–148° C., 0.35 torr) to provide 1031.1g (1.90 mole, 77.9% yield) of 4,4'-bis(2-bromotetrafluoroethoxy)biphenyl, melting point 71°–73° C. The Infrared (IR) spectra of the product has the following peaks ($cm^{-1}$): 1601,1492 (indicating an aromatic double bond); 1199–1107 (indicating carbon-oxygen and carbon fluorine bonds): 842, 788 (indicating aromatic character). The gas chromatograph/mass spectrometer (GC/MS) indicates peaks at the following mass to charge ratios: (m/e) =545 (29.8%): 543 (48.9%); 541 (23.8%): 365 (48.7%): 363 (50.9%); 337 (30.3%); 335 (34.7%); 168 (33.7%): 156 (78.3%): 140 (36.7%): 139 (90.1%): 129 (37.4%): 128 (100.0%): 127 (33.2%): 102 (32.9%); 76 (41.1%): 63 (34.3%), consistent with a product of 4,4'-bis(2-bromotetrafluoroethoxy)biphenyl.

Bromine is eliminated from this product by the following procedure:

Into a 1-liter 5-necked flask equipped with a mechanical stirrer, a thermocouple attached to a temperature controller, a powder addition funnel and a reflux condenser, is placed freshly distilled diglyme (200 ml) and fresh zinc powder (36.0g, 0.55 mole).

The mixture is stirred and heated to 130° C. Powdered 4,4'-bis(2-bromotetrafluoroethoxy)biphenyl (100g, 0.184 mole) is added very slowly via the powder addition funnel over 3.5 hours. The mixture is then stirred mechanically at 115° C. for 1 hour, after which, heating is turned off and the mixture is allowed to cool to room temperature. The solution is centrifuged to remove the zinc salts. Then the liquid is decanted, and the zinc salts are washed with acetone and centrifuged again. The liquid portions are combined and evaporated thoroughly, and the residue is dissolved in methylene chloride and washed with 0.05 M hydrochloric acid. The methylene chloride solution is evaporated to provide 62.45g (0.180 mole) of 4,4'-bis(trifluorovinyloxy)-biphenyl of 94.5% purity in 98% yield.

The product is then recrystallized in ethanol to give product of 99.99% purity in greater than 70% recovery, melting point 44°-46° C.

The IR spectrum shows peaks at (cm$^{-1}$): 1833 (indicative of a perfluorovinyl group): 1601,1491 (indicative of an aromatic double bond): 1231, 1196–1132 (indicative of carbon-oxygen and carbon-fluorine bonds respectively); 818 (indicative of aromaticity).

The GC/MS spectrum has the following peaks: m/e: 346 (31.3%): 153 (13.8%); 152 (100.0%): 151 (27.0%) 150 (11.7%); 76 (14.9%): 63 (14.9%).

Differential scanning calorimetry (DSC) analysis of the 4,4'-bis(trifluorovinyloxy)biphenyl monomer (20° C. to 360° C. at 20° C./minute) indicates a sharp endotherm of melting beginning at 45° C., followed by a broad exotherm beginning at about 170° C., interpreted as corresponding to the heat of cyclization of the trifluorovinyl groups to form hexafluorocyclobutane rings.

Monomer, 4,4'-bis(trifluorovinyloxy)biphenyl, (60.0g, 0.173 mole) is placed in a 1 liter 3-necked round bottom flask with 75 ml of perfluorotetradecahydrophenanthrene (Multifluor® APF 215 commercially available from Air Products). The flask is fitted with a mechanical stirrer and a nitrogen padded reflux condenser. After purging the flask thoroughly with nitrogen, the mixture is stirred and heated to reflux. Initially, upon heating the melted monomer is not miscible with the solvent, but as the temperature rises the two phases become homogeneous. After stirring at reflux for approximately 45 minutes, a polymer phase separates: and, after stirring at reflux for a total of 3 hours, the phase separated polymer becomes viscous enough to seize the stirring shaft. The cooled polymer is removed from the flask and evaporated under high vacuum (approximately 0.50 torr) at about 220° C. for 3 hours to remove residual solvent. A portion of this polymer is compression molded at 250° C. to provide a light yellow, transparent flexible plastic film. Another portion is dissolved in tetrahydrofuran (THF) and placed in an evaporating dish to make a solvent-cast film. After the solvent is evaporated overnight, a light yellow thin film is peeled from the dish. This sample exhibits excellent flexibility and transparency.

An IR spectrograph of the film has the following peaks (cm$^{-1}$): 1601, 1490 (indicating aromatic double bonds): 1302, 1194–1115 (indicating carbon-oxygen and carbon-fluorine bonds), 818 (indicating aromaticity).

DSC analysis of this polymer indicates a Tg transition at 148° C.

Dynamic mechanical analysis (DMS) gives a Tg value of 170°, and gel permeation chromatography (GPC) indicates a weight average molecular weight of 85,000 as standardized against polystyrene.

Dielectric constant and dissipation factor measurements performed on this polymer give the following results:

| Frequency (kHz) | Dielectric Constant | Dissipation Factor |
| --- | --- | --- |
| 1.01 | 2.58 | 0.0007 |
| 10.0 | 2.57 | 0.0004 |
| 1000.0 | 2.55 | 0.0004 |

A sample plaque of the biphenyl perfluorocyclobutyl ether polymer (12 cm×8 cm×1 cm) is placed inside a baking dish in a vacuum drying oven and is cured under vacuum at 310° C. for 20 hours. The sample is removed, and a coupon is cut (6.0 cm×1.2 cm×0.33 cm) for dynamic mechanical analysis. The analysis shows a Tg of 175° C. with no complete melt occurring, as is evidenced by maintenance of a storage modulus up to and including 344° C. This cured (crosslinked) polymer also does not dissolve in THF but swells into a gel.

A sample of the thermoplastic biphenyl perfluorocyclobutyl ether polymer is placed in a Rheometrics RMS-605 Mechanical Spectrometer using 25 mm parallel plates with a 1 mm gap. Using a 10% strain, storage and loss moduli are measured from 0.1 to 100 radians per second, measuring ten different frequencies per decade of frequency, every 15 minutes. Isothermal measurements are carried out according to the technique of H. H. Winter and F. Chambon, *J. Rheology*, 30(2), 367–382 (1986) except that the gel points are measured at 320° C. and 360° C. The log of tan delta (G''/G'), that is the logarithm of the ratio of the loss modulus (G'') to the storage modulus (G'), is plotted against time for various frequencies. A gel point is indicated by convergence of the various frequency dependent tan deltas in the plot at 15 minutes. A second experiment is run under similar conditions, but at 320° C. isothermal; a plot of tan delta against time indicates a gel point at 80 minutes. Furthermore, samples after being heated beyond the gel points are not soluble in tetrahydrofuran. Thus, the system appears to crosslink in 15 minutes at 360° C. and in 80 minutes at 320° C. Crosslinked samples exhibit some reddish brown or yellow color.

Physical property determinations on samples of the thermoplastic (uncrosslinked) polymer and on the crosslinked polymer show significant differences as indicated in the table below:

| Physical Property Comparison | | |
| --- | --- | --- |
| | Thermoplastic Polymer | Crosslinked Polymer |
| Tensile Strength[1] | 5,500 psi | 7,200 psi |
| Tensile Modulus[1] | 200,000 psi | 255,000 psi |
| Percent Elongation[1] | 12% | 4% |
| Flexural Strength[2] | 10,800 psi | 8,700 psi |
| Flexural Modulus[2] | 234,000 psi | 315,000 psi |
| Dielectric Constant[3] | 2.57 (10 kHz) | 2.59 (10 kHz) |
| Dissipation Factor[3] | 0.0004 (10 kHz) | 0.0006 (10 kHz) |

[1] As determined by the procedures of ASTM D882-83.
[2] As determined by the procedures of ASTM D790-81.
[3] As determined by the procedures of ASTM D150-87.

This data shows that crosslinking increases tensile strength and modulus as well as flexural modulus while reducing elongation without substantial change in electrical properties.

EXAMPLE 2

PREPARATION, SOLUTION POLYMERIZATION AND CROSSLINKING OF 9,9-BIS(4'-TRIFLUOROVINYLOXY]PHENYL)-FLUORENE

Into a 2 liter 5-necked round bottom flask fitted with a mechanical stirrer, Dean-Stark trap topped with a nitrogen padded reflux condenser and a thermocouple attached to a temperature controller, are placed DMSO (650 ml) and toluene (200 ml). While the stirred solution is purged with nitrogen, 9,9-bis(4'-hydroxyphenyl)fluorene (200.0g, 0.57 mole) is added to the flask. While purging with nitrogen continues, potassium hydroxide (85% pellets, 77.5g, 1.17 mole) is added all at once, and the mixture is heated to 100° C. with constant stirring. After two hours, the temperature is increased until the solution begins to reflux (130° C.). Water is removed by azeotropic distillation for 24 hours. The Dean-Stark trap is replaced by a Soxhlet extractor containing anhydrous sodium sulfate, and the toluene is refluxed through the Soxhlet for 5 hours. A small amount of toluene (60 ml) is then removed by simple distillation. Then the reactor is cooled to 35° C. Addition of 1,2-dibromotetrafluoroethane (315g, 1.21 mole) via dropping addition funnel is then maintained at a rate that keeps the reaction temperature at 35°–38° C. When the addition is complete, the mixture is heated at 50° C. for 8 hours, then cooled to room temperature with constant stirring. The mixture is filtered, and the precipitate is washed twice with acetone. The filtrates are combined and evaporated thoroughly. The residue from the evaporation is washed with water to remove residual potassium bromide (KBr). After the residue is air dried for 24 hours, it is purified by column chromatography (on neutral alumina, using hexane eluent) to provide as product, 9,9-bis(4'-[2''-bromotetrafluoroethoxy]-phenyl)fluorene (331.4g, 0.468 mole, 82% yield), melting point 157°–158° C.

The LC/MS spectrum has peaks at: m/e: 710 (53.0%): 709 (34.0%): 708 (100.0%): 707 (23.3%): 706 (49.8%); 513 (28.4%); 511 (28.5%): 438 (12.8%): 437 (52.4%): 436 (14.7%): 435 (55.8%); 355 (15.7%): 290 (33.9)%: 289 (19.5%): 239 (35.9%): 228 (36.2%): 227 (38.9%): 226 (47.3%): 202 (27.7%): 157 (47.2%); 131 (27.6%): 129 (23.1%).

The product from the above reaction (18.85 g, 0.027 mole) is combined with freshly activated granular zinc (5.00g, 0.076 mole) in glyme and heated at reflux overnight. After cooling, the reaction mixture is decanted and centrifuged to remove suspended zinc salts. The solvent is removed by vacuum evaporation, and the residue is purified by column chromatography on neutral alumina using hexane as an eluent to provide as product 9,9-bis(4'-trifluorovinyloxyphenyl)fluorene (5.55 g, 011 mole, 40% yield), melting point 115°–116° C.

The LC/MS spectrum has peaks at: m/e: 511 (29.3%): 510 (91.9%): 337 (37.2%): 316 (16.1%): 315 (19.7%); 313 (12.8%); 241 (15.5%); 240 (52.8%): 239 (100.0%): 237 (15.6%): 207 (14.1%): 158 (28.7%): 157 (53.1%): 155 (14.4%): 150 (28.8%): 145 (18.3%): 144 (16.5%): 120 (15.1%).

Into a 50 ml round bottom flask fitted with a nitrogen padded reflux condenser, mechanical stirrer and a thermocouple attached to a temperature controller are placed 9,9-bis(4'-trifluorovinyloxyphenyl)fluorene (3.0g, 0.0059 mole) and diphenyloxide (5.0 ml). The mixture is stirred and heated to reflux (255° C.) for 22 hours. The diphenyloxide (DPO) solvent is evaporated under high vacuum on a 100 milliliter Kugelrohr bulb to bulb apparatus (0.03 mm, 165° C.) to provide the polymer product, which is dissolved in methylene chloride and cast into a thin film.

Gel permeation chromatography analysis of the polymer indicates a weight average molecular weight of 135,000 as standardized against polystyrene.

DSC analysis indicates a Tg transition at 224° C.

It is notable that this polymer of 9,9-bis (4,4'-trifluorovinyloxyphenyl)fluorene, which is polymerized in DPO, attains a high molecular weight and forms a solvent cast film with good physical properties such as flexibility. The polymer is soluble in acetone, dichloromethane and tetrahydrofuran.

A sample of the 9,9-bis(4'-oxyphenyl)fluorene perfluorocyclobutyl ether polymer is placed in the Rheometrics RMS-605 Mechanical Spectrometer using the conditions of Example 1. A plot of the tan delta against time for a 360° C. isothermal experiment indicates a gel point in less than 10 minutes. A similarly run experiment at 320° C. isothermal indicates a gel point in 35 minutes.

These gel points are indicative of curing of the samples into crosslinked polymer systems. Thus, the system appears to crosslink in less than 10 minutes at 360° C. and in 35 minutes at 320° C. Samples of the polymer heated to the gel point are insoluble in acetone, dichloromethane and tetrahydrofuran. The Tg is measured by differential scanning calorimetry to be 240° C.

EXAMPLE 3

PREPARATION, POLYMERIZATION AND CURING OF 2,2-BIS((4-PERFLUOROVINYLOXY)PHENYL)-PROPANE

The procedure for preparing the diperfluorovinyl compound of Example 1 is followed except that smaller scale equipment is used with about half the amounts of solvent for the various steps using 100.0g, 0.44 mole of para-bisphenol A in place of the 4,4'-dihydroxybiphenyl; 59.0g, 0.89 mole of potassium hydroxide pellets: 240g, 0.92 mole of 1,2-dibromotetrafluoroethane; and 25.0g, 0.38 mole of granular zinc. The toluene mixture is heated to reflux (125° C.). Water is removed by azeotropic distillation for a total of 48 hours, without cooling after 24 hours. Before addition of the 1,2-dibromotetrafluoroethane, the toluene is dried by refluxing through the extractor for 20 hours. After cooling to room temperature the reaction flask is cooled to 18° C. in an ice bath. The 1,2-dibromotetrafluoroethane is added at a rate that maintains a reaction temperature of 18°–22° C. Then the mixture is allowed to warm to room temperature, and is heated slowly to 50° C. and stirred at 50° C. for 6 hours.

A crude reaction mixture forms and is filtered. The filtrate is evaporated thoroughly leaving a residue which is chromatographed on neutral alumina (50–200 mesh) using hexane as eluent to provide 113.9g (44% yield) of a product having a GC/MS with peaks at the following mass to charge ratios (m/e): 587 (4.6%): 585 (9.2%): 583 (5.0%): 572 (44.5%): 570 (100%): 568

(52.0%): 397 (11.3%); 395 (11.0%): 315 (27.1%): 313 (28.2%): 299 (28.0%): 297 (30.4%): 181 (31.1%), 179 (37.6%); 167 (29.1%): 165 (37.8%): 131 (33.6%); 129 (36.9%): 115 (32.4%); 101 (35.7%): 91 (31.3%): 77(33.5%) consistent with a bisphenol A bis(2-bromotetrafluoroethyl) ether, 99+% pure by GC/MS analysis.

After reaction with the granular zinc at 105° C., the bisphenol A bis(2-bromotetrafluoroethyl) ether (103.4g, 0.176 mole) is placed in a 100 ml dropping addition funnel and added at a rate that maintains a reaction temperature of 105°–108° C. When the addition is complete the mixture is stirred at 108° C. for 2.5 hours, then cooled to room temperature. The mixture is centrifuged to remove the solids; the precipitate is separated and washed with acetone and again separated by centrifuging. The liquid portions are combined and evaporated leaving a residue which is chromatographed through a neutral alumina column using hexane as an eluent to provide 42.8g (63% yield) of a product having a GC/MS with peaks at the following mass to charge ratios (m/e): 388 (17.5%): 374 (20.0%): 373 (100%): 276 (30.4%); 215 (46.7%); 199 (12.8%): 179 (24.8%): 178 (50.0%): 152 (15.6%): 118 (24.0%): 117 (18.3%): 115 (17.1%): 102 (19.9%): 89 (23.5%): 77 (22.6%): 76 (29.9%) bisphenol A bis(trifluorovinyl) ether.

The bisphenol A bis(trifluorovinyl) ether monomer (13.6g) is combined with 14.0 ml of Multifluor APF 215 solvent in a 100 ml 3-necked round bottom flask fitted with a mechanical stirrer and a nitrogen padded reflux condenser. Stirring is begun as the mixture is heated to reflux. The mixture is stirred at reflux for 5 hours, then allowed to cool to room temperature. A layer of polymer phase-separates to the top of the solvent. This polymer is removed and evaporated at 180° C. under high vacuum (0.15 torr) to remove residual solvent.

A sample of the polymer is placed in the Rheometrics RMS-605 Mechanical Spectrometer using the conditions used in Example 1. A plot of the tan delta against time for a 360° C. isothermal experiment indicates a gel point in 50 minutes. A similar experiment at 320° C. isothermal indicates that no gel point is reached by this polymer in the 150 minute time span of the experiment. These rheological experiments indicate that crosslinking of this polymer is much slower.

What is claimed is:

1. A process for preparing a crosslinked polymer having perfluorocyclobutane rings comprising the steps of:
    (a) contacting monomers having two dimerizable perfluorovinyl groups;
    (b) exposing the monomers to sufficient heat and for a sufficient time that a polymer containing perfluorocyclobutane rings is formed: and
    (c) exposing the polymer to sufficient crosslinking initiating means and for a sufficient time such that crosslinking occurs and a crosslinked polymer is produced.

2. The process of claim 1 wherein the crosslinking of step (c) reduces the percent elongation as measured by the procedure of ASTM D790-81 by at least about 10 percent of the percent elongation measured for the polymer produced in step (b).

3. The process of claim 2 wherein the crosslinking initiating means is a means of providing free radicals.

4. The process of claim 2 wherein the crosslinking takes place substantially without addition of a crosslinking agent or catalyst.

5. The process of claim 4 wherein the crosslinking initiating means is wave energy.

6. The process of claim 4 wherein the crosslinking initiating means is heat.

7. The process of claim 6 wherein the heat is radiant heat.

8. The process of claim 6 wherein the polymer reaches a gel point in less than about 2 hours at 360° C.

9. The process of claim 8 wherein the polymer reaches a gel point in less than about 2 hours at 320° C.

10. The process of claim 9 wherein the polymer reaches a gel point in less than about 2 hours at 280° C.

11. The process of claim 6 wherein the crosslinking step takes place at a temperature at least about 50° C. higher than the temperature used in step (b).

12. The process of claim 11 wherein the crosslinking step takes place at a temperature of from about 250° C. to about 400° C.

13. The process of claim 12 wherein the crosslinking step takes place at a temperature of from about 280° C. to about 380° C.

14. The process of claim 13 wherein the crosslinking step takes place at a temperature of from about 280° C. to about 340° C.

15. The process of claim 12 wherein the crosslinking step (c) takes place in a shaping apparatus.

16. The process of claim 12 wherein the tensile strength as measured by the procedure of ASTM D882-83 of the crosslinked polymer produced in step (c) is from about 10 to about 500 percent greater than that of the corresponding polymer produced in step (b).

17. The process of claim 12 wherein the tensile modulus as measured by the procedure of ASTM D882-83 of the crosslinked polymer produced in step (c) is from about 10 to about 500 percent greater than that of the corresponding polymer produced in step (b).

18. The process of claim 12 wherein the flexural modulus as measured by the procedure of ASTM D790-81 of the crosslinked polymer produced in step (c) is from about 10 to about 500 percent greater than that of the corresponding polymer produced in step (b).

19. The process of claim 1 wherein the monomers have a structure represented by Formula I:

$$CF_2=CF-X-R-X-CF=CF_2$$

wherein R represents an unsubstituted or inertly substituted hydrocarbyl group: and each X is independently selected from the group consisting of groups having at least one non-carbon atom between R and $-CF=CF_2$.

20. The process of claim 19 wherein X is selected from the group consisting of oxygen atoms, sulfur atoms, sulfoxide, sulfone, carbonyl, thiocarbonyl and silanediyl groups.

21. The process of claim 20 wherein R is an unsubstituted or inertly substituted group which reacts with perfluorovinyl groups residual in a substantially linear polymer to form a crosslinked or branched molecular structure.

22. The process of claim 21 wherein R includes a structure having at least two multiple bonds separated by a single bond.

23. The process of claim 22 wherein R includes at least one biphenyl group.

24. The process of claim 22 wherein each X is independently an oxygen atom, a sulfur atom, a sulfoxide group, or a sulfone group.

25. The process of claim 24 wherein the single bond is a carbon to carbon single bond.

26. The process of claim 25 wherein at least one of the multiple bonds is a bond between carbon and any other atom.

27. The process of claim 26 wherein at least one of the multiple bonds is a carbon to carbon bond.

28. The process of claim 27 wherein at least two of the multiple bonds are carbon to carbon bonds.

29. The process of claim 28 wherein at least one of the multiple bonds is a carbon to carbon double bond.

30. The process of claim 29 wherein at least two of the multiple bonds are carbon to carbon double bonds or aromatic bonds.

31. The process of claim 30 wherein R is an unsubstituted or inertly substituted biphenylene; phenylene: 9,9'-diphenylfluorene: fluorene; cyclopentadienylene; furan: or anthracene group.

32. The process of claim 1 wherein the polymer containing perfluorocyclobutane rings has perfluorocyclobutane rings in the backbone of the polymer.

* * * * *